United States Patent [19]

Wentzell

[11] Patent Number: 4,581,955

[45] Date of Patent: Apr. 15, 1986

[54] REACTOR COOLANT PUMP MOTOR ROTATOR

[75] Inventor: Timothy H. Wentzell, South Windsor, Conn.

[73] Assignee: Combustion Engineering, Inc., Windsor, Conn.

[21] Appl. No.: 559,610

[22] Filed: Dec. 8, 1983

[51] Int. Cl.$^4$ ............................................. B25B 17/00
[52] U.S. Cl. ................................. 81/57.13; 81/57.15; 81/57.29
[58] Field of Search .................. 81/57.11, 57.13, 57.2, 81/57.29, 57.46, 57.17, 57.15

[56] References Cited

U.S. PATENT DOCUMENTS

| | | | |
|---|---|---|---|
| 1,031,261 | 7/1912 | Helm | 81/57.15 |
| 1,400,067 | 12/1921 | Hughes | 81/57.15 |
| 1,462,377 | 7/1923 | Painter et al. | 81/57.15 |
| 2,509,853 | 5/1950 | Wilson | 81/57.15 |
| 2,846,909 | 8/1958 | Mason | 81/57.2 |
| 3,023,651 | 3/1962 | Wallace | 81/57.2 |

Primary Examiner—James L. Jones, Jr.
Attorney, Agent, or Firm—Arthur E. Fournier, Jr.

[57] ABSTRACT

A device (10) particularly suited for use for purposes of effecting the rotation of a reactor coolant pump motor (12) and flywheel (18) when the latter is required to be rotated, as for instance, in order to accomplish an ultrasonic and eddy current examination of the flywheel (18). The subject device includes housing means (20) of a multipartite construction capable of being secured in surrounding relation to the shaft (16) of the pump (12). Within the housing means (20) there is provided ball bearing means (26) and driven gear means (28). In addition, the subject device (10) also includes drive motor means (30) that is operatively associated with a drive gear means (36). The latter drive gear means (36) of the drive motor means (30) is supported in cooperative relation with the driven gear means (36) of the housing means (20) such that rotation of the drive motor means (30) is imparted to the drive gear means (36) and therefrom to the drive gear means (28). In turn, the rotation of the driven gear means (28) is imparted to the shaft (16) of the pump (12) thereby causing the rotation also of the pump motor (12) and flywheel (18), and hence enabling the desired examination of the flywheel (18) to be had.

3 Claims, 6 Drawing Figures

REACTOR COOLANT PUMP MOTOR ROTATOR

BACKGROUND OF THE INVENTION

This invention relates to apparatus for effecting the rotation of a device, and more specifically, to a rotator operative for accomplishing the rotation of a reactor coolant pump and flywheel such that an examination by ultrasonic and/or eddy current means may be had of the flywheel.

There are known to exist many instances wherein it is desirable and/or necessary to effect an examination, and in particular a surface examination, of an operating component. Notwithstanding the number of such instances and the differences that exist therebetween, in general one finds that the reason for conducting such an examination is associated in some manner with the need to determine the relative operating condition of the component in question. That is, commonly there exists a need to ensure the operability of the component preparatory to its being placed in service and/or the need periodically to certify that the component is still in good working order. To this end, it is not uncommon to find that standards have been promulgated in this regard for various kinds of operating components. Namely, these standards, which have been promulgated, serve to establish the nature and/or extent of the defects, which will be deemed to render a particular type of operating component unserviceable.

By way of exemplification and not limitation, reference is had here to rotary members, as being representative, generally, of one such form of component. Further, one specific type of rotary member to which reference may be made in this connection is that of flywheels, and in particular flywheels of the sort, which often are found cooperatively associated with the coolant circulation pump motors that are employed in nuclear steam supply systems. The function which flywheels perform in this type of a nuclear-related application is that of assisting in the accomplishment of coastdown of the coolant circulation pump motors. As such, it is, therefore, important that when the flywheels are needed that they be capable of functioning in their intended manner. To this end, obviously one way of ensuring that the flywheels are in good working order is to periodically conduct an examination of the flywheels for defects. Moreover, rather than depending on compliance with some voluntary schedule of examination of such components, it is known that in a number of instances governmental authorities have promulgated regulations that mandate the performance of such periodic examination with regard to particular components for purposes of effecting a detection of defects therein that could impair the operativeness of the component. This is particularly true in the case of many of the operating components of a nuclear steam supply system.

With specific regard to flywheels of the sort referred to above, i.e., the large flywheels needed for coastdown in nuclear reactor coolant circulation pump motors, existing governmental regulations require that they undergo surface examinations during preservice and at ten year intervals during the life of the nuclear plant in which they are installed. Note is taken here of the fact that in requiring that surface examinations be performed on such flywheels, governmental regulations have not only specified the frequency of such examinations and the nature of the defects which the surface examination was intended to detect, but have also dictated the manner in which the examination is to be performed. Namely, such governmental regulations have heretofore required that the surface examination be conducted in accordance with the procedures that are found set forth in the applicable industrial codes, which have been promulgated governing the performance of surface examinations of metal components.

By way of exemplification in this regard, one method that has been found suitable for use for purposes of performing a surface examination of a coated component such as the flywheel associated with the coolant circulation pump motor employed in a nuclear power generation system forms the subject matter of co-pending U.S. Patent Application Ser. No. 266,397, now U.S. Pat. No. 4,418,315, which was filed in the name of Lawrence J. Edwards and John P. Lareau, and which is assigned to the same assignee as the present application. The method which forms the subject matter of the aforereferenced U.S. patent has been deemed to be acceptable under the applicable industrial codes as a technique which is recognized for use for the purpose of surface examinations of metal components. As described in the aforementioned U.S. patent, the subject method includes the steps of providing a calibration block embodying characteristics similar to the component that is to undergo the surface examination and having a plurality of crack-like notches formed in a surface thereof, providing a layer-like film of nonmetallic material embodying characteristics similar to the coating borne by the component that is to undergo the surface examination, positioning the layer-like film of nonmetallic material in superimposed relation on the calibration block so as to cover the plurality of crack-like notches formed in the calibration block, establishing with eddy current means calibration readings from the calibration block having the layer-like film of nonmetallic material positioned in superimposed relation thereto, performing a surface examination of the coated metal component with the eddy current means by moving the eddy current means over the surface of the coated metal component in a traversing pattern corresponding to the pattern defined by the plurality of scribe lines provided on the layer-like film of nonmetallic material, and comparing the readings obtained from the surface examination of the coated metal component with the calibration readings obtained from the calibration block to establish the presence of any cracks of at least a minimal dimension in the surface of the coated metal component. In the case of many known methods for performing a surface examination of a component, including the method described in this paragraph, there is a need in order to satisfactorily accomplish the examination therewith that relative motion be made to take place between the component, which is the subject of the examination, and the means with which the examination is being conducted. More specifically, in accord with some of the known methods for performing a surface examination of a component, the means by which the examination is conducted is required to be made to move relative to the component undergoing examination. While yet on the other hand, other methods for performing a surface examination of a component require that the component being examined be moved relative to the means, which is being utilized in the conduct of the examination.

As concerns those methods of examining components wherein there is a requirement that the component undergo movement in order to accomplish the examination thereof, the manner in which this movement of the component is effectuated is of prime importance to the successful performance of the examination. In this regard, it is of prime importance that consideration be given to factors, which by way of exemplification and not limitation, include items such as the following: the weight and size of the component, the ease of accessibility to the component, the nature of the movement be it rotational or translational which the component is required to undergo, the consistency of the movement required in terms of the deviation permitted from a given mean, the repeatability required as between subsequent tests, etc.

Continuing, with regard, for instance, to the matter of weight and size, the component which is to undergo the subject examination may be so heavy and/or have such large dimensions that it would be virtually impossible to manually impart thereto the movement desired. On the other hand, insofar as accessibility is concerned, the location of the component to be examined may be such as to preclude the use of some form of mechanical means to impart movement thereto. In terms of whether the component being examined is required to undergo rotational or translational motion, normally it would be possible to impart either of those types of motion to the component either manually or through some suitable form of mechanical means. In those instances wherein consistency and repeatability are required, the use of some form of mechanical means to impart movement to the component in question would most often be necessitated.

Attention will now be focused on a specific application wherein a need exists to impart movement to a component for purposes of performing an examination thereof. More specifically, reference is had here to coolant pumps of the type that one finds being employed in a nuclear steam supply system. With respect to such pumps, a requirement exists that they undergo examination. This examination commonly takes the form of an ultrasonic and eddy current examination of the flywheel that is cooperatively associated with the pumo motor. Moreover, in order to accomplish this examination the flywheel and pump motor must be rotated. Heretofore, for purposes of accomplishing this rotation of the flywheel and pump motor the practice has been to effect this rotation manually. That is, although the force that is required to be applied in order to accomplish the desired rotation of the flywheel and pump motor has normally been found to be of greater magnitude than a person is capable of exerting without assistance, by making use of the mechanical advantage that can be derived from the employment of a mechanical device such as a lever, it has been possible to manually accomplish the desired rotation of the flywheel and pump motor. However, though it has been possible in this manner to effect the rotation of the flywheel and pump motor, a less cumbersome and more efficient method has been sought for accomplishing this purpose. Accordingly, a need has thus been evidenced in the prior art for a new and improved apparatus suitable for use for purposes of effecting the rotation of a component such as a reactor coolant pump motor and flywheel, and one which is particularly useful when the rotation desired is necessitated by the need to subject the component to an examination, as for example, of an ultrasonic and eddy current nature.

It is, therefore, an object of the present invention to provide a new and improved apparatus operative for purposes of effecting relative motion between a component and another device.

It is another object of the present invention to provide such an apparatus which for purposes of effecting relative motion between a component and another device is operative to impart rotation to the component.

It is still another object of the present invention to provide such an apparatus which is particularly suited for use for purposes of imparting rotation to a component wherein the component is required to be rotated in order to conduct an examination thereof.

A further object of the present invention is to provide such an apparatus which is particularly suited for use for purposes of effecting the rotation of a reactor coolant pump motor and flywheel in order that an examination may be conducted thereof.

A still further object of the present invention is to provide such an apparatus operative for purposes of imparting rotation to a reactor coolant pump motor and flywheel wherein the apparatus is characterized in that a constant speed of rotation is capable of being imparted therewith.

Yet another object of the present invention is to provide such an apparatus operative for purposes of imparting rotation to a reactor coolant pump motor and flywheel wherein the apparatus is characterized in that it is relatively easy to install, relatively simple to operate, yet is relatively inexpensive to provide.

SUMMARY OF THE INVENTION

In accordance with the present invention, there is provided an apparatus, which is particularly suited for use for purposes of effecting the rotation of a component. More specifically, the subject apparatus is particularly suited for use for purposes of effecting the rotation of a reactor coolant pump motor and flywheel, when the latter is required to be rotated, as for instance, in order to accomplish an ultrasonic and eddy current examination of the flywheel. The subject apparatus includes a housing formed in segments and suitably dimensioned so as to be capable of being mounted in surrounding relation to the shaft of the pump motor. Preferably, a non-marring friction wrap encircles the pump motor shaft at the location therealong whereat the aforesaid housing is mounted on the pump motor shaft. The housing in turn suitably embodies ball bearing means and driven gear means. The latter driven gear means is designed to be cooperatively associated with a gear head electric drive motor means whereby, in order to effect the rotation of the pump motor and flywheel, rotation is imparted from the drive motor means to the driven gear means and therethrough to the pump motor shaft. This is accomplished by virtue of the fact that the inner diameter bearing race is common with the driven gear and the outer diameter bearing race is common with the drive motor such that relative motion can be made to occur therebetween. Lastly, turning of the outer diameter bearing race and drive motor is resisted through the use of an antirotation means with which the subject apparatus is preferably suitably provided.

DESCRIPTION OF A PREFERRED EMBODIMENT

Figure 1:
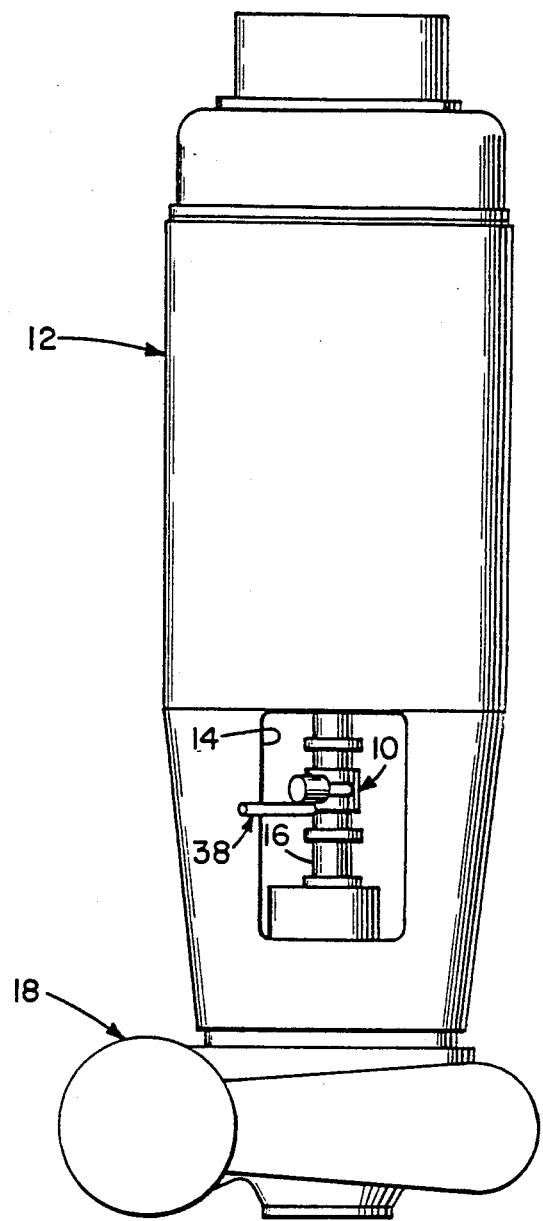
FIG. 1 is a plan view of a reactor coolant pump motor and flywheel illustrated with an apparatus, constructed in accordance with the present invention, operative for purposes of imparting rotation to the pump motor shaft and flywheel, positioned in mounted relation on the pump motor shaft.
Figure 3:
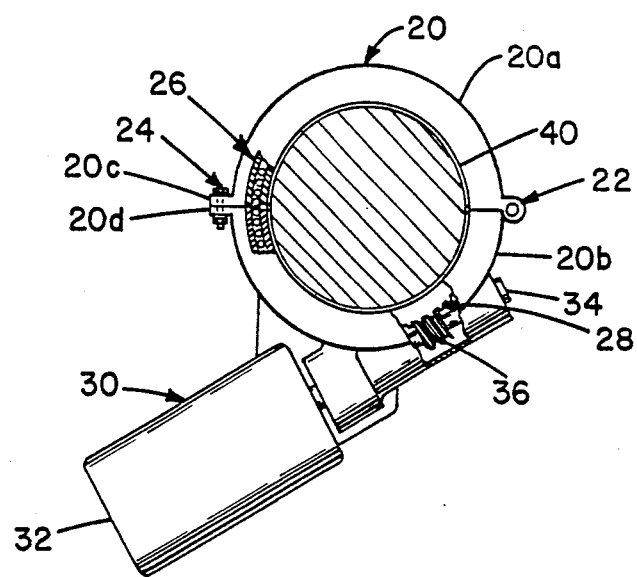
FIG. 3 is an end view with some parts broken away of the apparatus of FIG. 1, constructed in accordance with the present invention, operative for purposes of imparting rotation to a reactor coolant pump motor shaft and the flywheel, illustrated positioned in mounted relation on the pump motor shaft.
Figure 2:
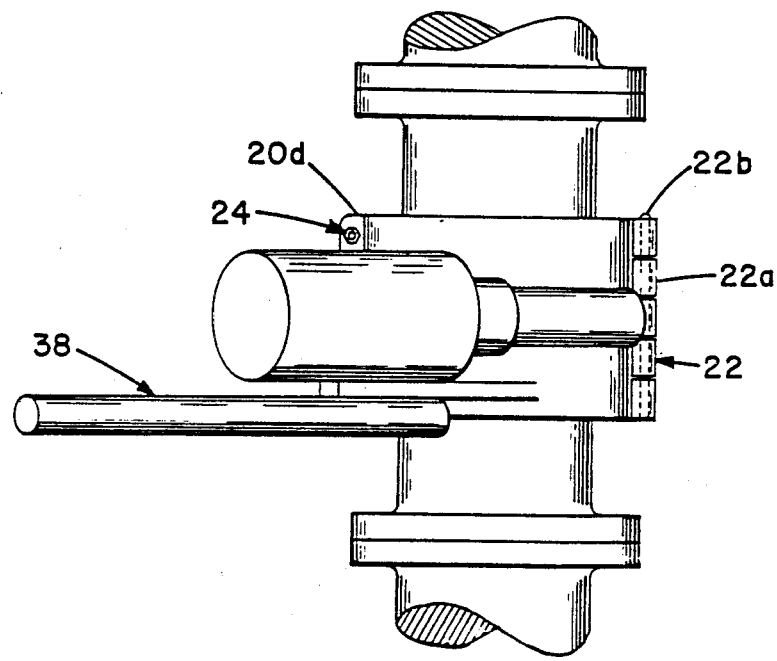
FIG. 2 is a side elevational view on an enlarged scale of the apparatus of FIG. 1, constructed in accordance with the present invention, operative for purposes of imparting rotation to a reactor coolant pump motor shaft and the flywheel, illustrated positioned in mounted relation on the pump motor shaft.

Referring now to the drawing, and in particular to FIGS. 1, 2 and 3 thereof, there is depicted therein an apparatus, generally designated by the reference numeral 10, constructed in accordance with the present invention. The apparatus 10 is operative for purposes of imparting rotation to a component. Moreover, by way of exemplification and not limitation, one such component to which rotation may be imparted through the use of the apparatus 10 is the reactor coolant pump motor depicted in FIG. 1, and denoted generally therein by the reference numeral 12.

For purposes of acquiring an understanding of the nature of the construction and the mode of operation of the apparatus 10, it is not deemed necessary either to illustrate in the drawing or to describe in detail herein the nature of the construction and/or mode of operation of the reactor coolant pump motor 12. Furthermore, since the reactor coolant pump motor 12 is of conventional construction, reference may be had to the prior art, should such a need arise, for a fuller illustration and/or description of the reactor coolant pump motor 12. However, insofar as the present invention is concerned, it is deemed to be sufficient simply to take note of the fact that the reactor coolant pump motor 12 is provided with a suitably dimensioned access port, shown at 14 in FIG. 1, through which access may be had to the shaft 16 of the reactor coolant pump motor 12, and that a flywheel, generally designated in FIG. 1 by the reference numeral 18, is affixed, through the use of any conventional form of means (not shown) suitable for this purpose, to one end of the shaft 16 so as to rotate therewith as a unit. As has been mentioned previously herein, when the reactor coolant pump motor 12 is being employed in a nuclear steam supply system, one of the primary functions that the flywheel 18 is intended to perform is that of effectuating coastdown of the reactor coolant pump motor 12.

Proceeding now with the description of the nature of the construction and the mode of operation of the apparatus 10, the latter as best understood with reference to FIGS. 2 and 3 of the drawing includes a housing 20. In accord with the illustrated embodiment thereof, the housing 20 is of multipartite construction. Namely, the housing 20, as shown in the drawing, preferably is comprised of two substantially semicylindrical segments 20a and 20b. Each of the segments 20a and 20b is suitably provided at one end thereof with hinge means, the latter being denoted generally in FIGS. 2 and 3 of the drawing by the reference numeral 22. The hinge means 22, which is of conventional construction, consists of a multiplicity of loop-like members 22a in which a pin-like member 22b is received. It is to be understood, however, that other forms of hinge means could equally well be employed in lieu of the hinge means 22 without departing from the essence of the invention. The hinge means 22 is designed to perform the dual functions of that of effecting the joinder of the segments 20a and 20b so that they are capable of functioning as a single unit, while yet enabling the segments 20a and 20b to pivot relative to each other about the hinge means 22 for a purpose yet to be described.

Referring again to the drawing and more particularly to FIG. 3 thereof, the segments 20a and 20b, as shown therein, are each provided at the other end thereof with an outwardly extending portion 20c and 20d, respectively. The portions 20c and 20d are each suitably dimensioned and configured so as to be capable of receiving therein in threaded engagement therewith the fastener means, which is denoted generally in FIGS. 2 and 3 of the drawing, by the reference numeral 24. The fastener means 24 comprises a plurality of threaded fasteners of conventional construction, only one of which is visible in each of FIGS. 2 and 3 of the drawing. As will be described more fully hereinafter, the fastener means 24 is operative to fasten the segments 20a and 20b together in encircling relation to a member such as the shaft 16 of the reactor coolant pump motor 12.

Within the housing 20 there is embodied ball bearing means, denoted generally in FIG. 3 by the reference numeral 26. More specifically, the ball bearing means 26 consists of a split ring ball bearing, which in turn includes an inner diameter bearing race and an outer diameter bearing race that in known fashion cooperate one with another such that relative motion can be made to occur therebetween. In addition, the housing 20 includes gear means, denoted generally by the reference numeral 28 in FIG. 3. The gear means 28 preferably comprises a two piece driven gear, with one piece thereof being associated with a corresponding one of each of the segments 20a and 20b of the housing 20. Accordingly, and in a manner to which further reference will be had hereinafter, when the segments 20a and 20b are clamped in encircling relation to a member such as the reactor coolant pump motor shaft 16, the gear means 28 is likewise caused to be clamped in encircling relation to the shaft 16.

Continuing, in a manner well-known to those skilled in the art and as will be best understood with reference to FIG. 3 of the drawing, there is cooperatively associated with the gear means 20a in operative relation thereto a gear head electric drive motor means, the latter being denoted generally by the reference numeral 30 in FIG. 3. The gear head electric drive motor means 30 encompasses the electric drive motor 32 from which there projects in an outwardly direction a shaft 34 on which gear means 36 is suitably mounted for rotation therewith. With the gear head electric drive motor means 30 positioned relative to the gear means 28 in the manner depicted in FIG. 3, the gear means 36 of the former engages the latter. To this end, the gears of the gear means 36 are suitably dimensioned and configured so as to mesh in known fashion with the gears of the two piece driven gear means 28 whereby the latter is capable of being driven by the former when rotation is imparted thereto from the electric drive motor 32 through the drive shaft 34.

For a purpose to which further reference will be had hereinafter, the apparatus 10 also includes antirotation means, denoted generally in FIGS. 1 and 2 of the drawing by the reference numeral 38. In accord with the best mode embodiment of the apparatus 10, the antirotation means 38 comprises a bar supported on the housing 20 in any suitable conventional fashion such that the bar 38 projects outwardly in a radial direction from the housing 20. Preferably, however, as depicted in FIGS. 1 and 2 of the drawing, the bar 38 is formed integrally with the housing 20 and extends outwardly therefrom so as to bear substantially a parallel relationship to the electric drive motor 32.

A description will now be had of the mode of operation of the apparatus 10. For this purpose, reference will be made in particular to FIGS. 1 and 3 of the drawing. In order to mount the apparatus 10 in operative relation on the shaft 16 of the reactor coolant pump motor 10, access is had thereto through the access port 14. More specifically, with the segments 20a and 20b of the housing 20 being unfastened one from another so as to be free to pivot about the hinge means 22, the apparatus 10 is passed into the interior of the reactor coolant pump motor 10 through the access port 14 thereof. The segments 20a and 20b are then suitably pivoted about the hinge means 22 so as to permit the seqments 20a and 20b to pass around the shaft 16 whereby the latter is encircled thereby. Preferably, however, and as best understood with reference to FIG. 3, a non-marring friction wrap denoted by the reference numeral 40 is wrapped around the shaft 16 such as to be positioned in interposed relation between the shaft 16 and the segments 20a and 20b encircling the latter. With the segments 20a and 20b so positioned relative to the shaft at the location therealong whereat the non-marring friction wrap 40 encircles the shaft 16, the segments 20a and 20b are suitably clamped in surrounding relation to the shaft 16 by means of the fastener means 24. As such the apparatus 10 bears the relationship to the shaft 16 depicted in FIG. 1 such that the electric drive motor shaft 32 and the antirotation bar 38 extend outwardly of the reactor coolant pump motor 12 through the access port 14 thereof.

Rotation of the shaft 16 can now be effected simply by energizing in conventional fashion the electric drive motor 32 whereby the shaft 34 associated therewith and on which the gear means 36 is mounted is caused to rotate. By virtue of the engagement of the gear means 36 with the gear means 28 the rotation of the former is imparted to the latter. Moreover, because the gear means 28 is common with the inner diameter bearing race of the split ring ball bearing means 26, whereas the outer diameter bearing race of the split ring ball bearing means 26 is common with the drive motor 32, relative motion is capable of being made to take place between the two races of the split ring ball bearing means 26. More specifically, the aforereferenced relative motion is occasioned by the inner diameter bearing race of the split ring ball bearing means 26 being made to move relative to the outer diameter bearing race of the split ring ball bearing means 26. While the inner diameter bearing race is free to rotate and thereby cause the shaft 16 to also rotate by virtue of the former being clamped thereabout, movement of the outer diameter bearing race of the split ring ball bearing means 26 is resisted by virtue of the action of the antirotation bar 38. Namely, the engagement of the antirotation bar 38 with the sidewall defining the opening that comprises the access port 14 serves to resist any tendency of the outer diameter bearing race of the split ring ball bearing means 26 to rotate and thereby any tendency of the drive motor 32 which is common therewith to rotate when rotation is being imparted to the inner diameter bearing race of the split ring ball bearing means 26 and therethrough to the shaft 16 of the reactor coolant pump motor 12.

Figure 4:
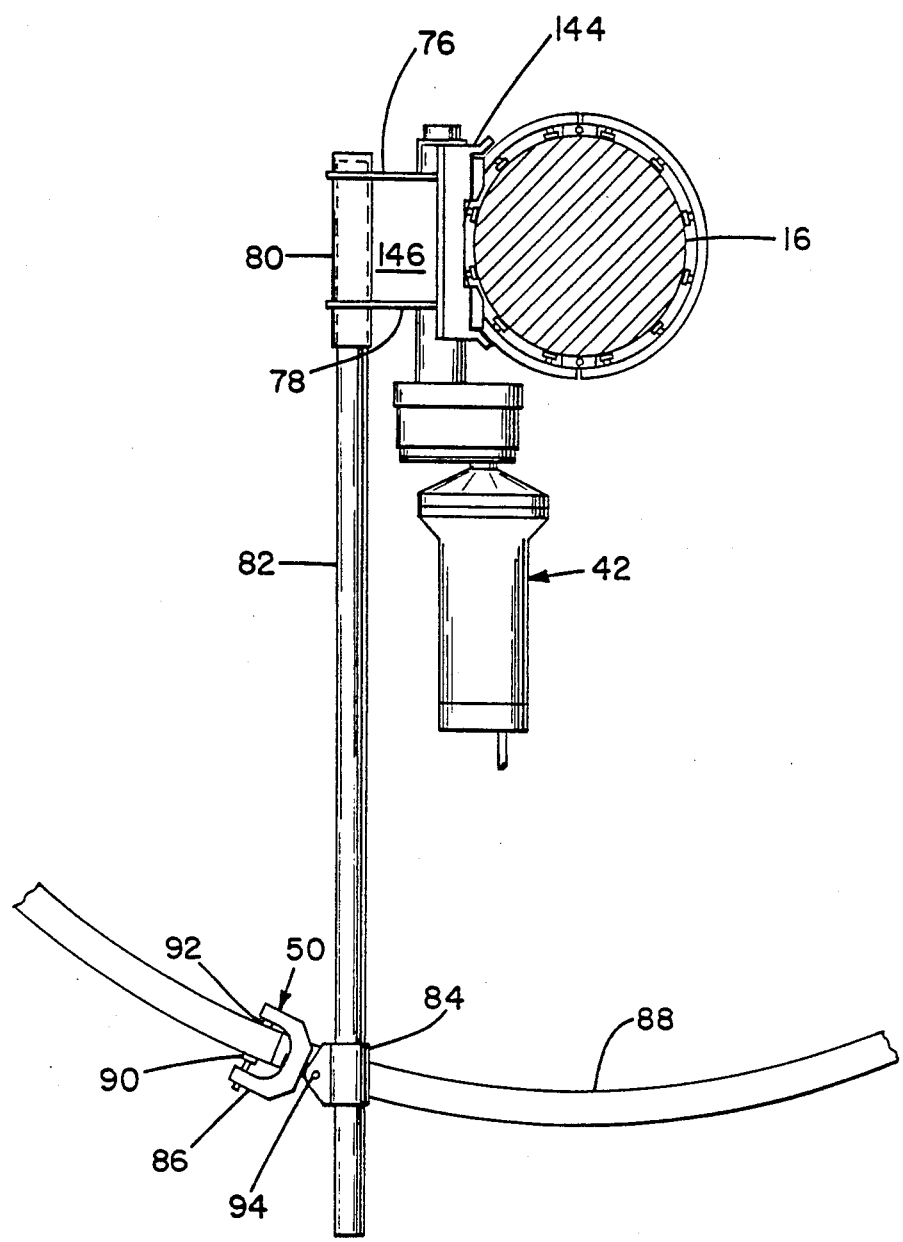
FIG. 4 is a side elevational view of another embodiment of an apparatus, constructed in accordance with the present invention, operative for purposes of imparting rotation to a reactor coolant pump motor shaft and the flywheel, illustrated positioned in mounted relation on the pump motor shaft.
Figure 6:
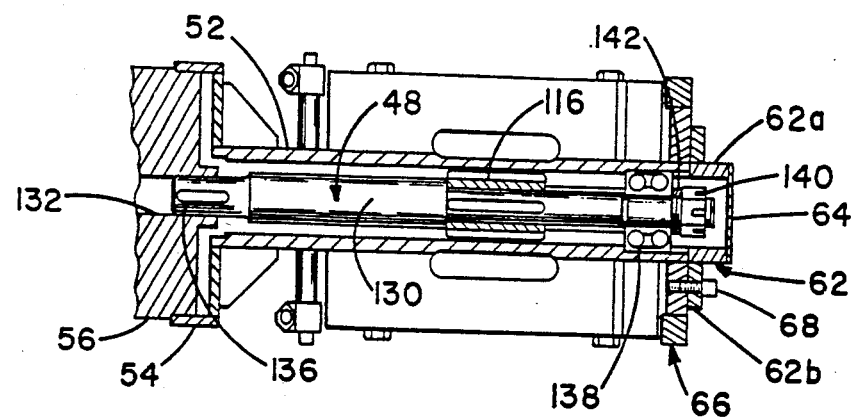
FIG. 6 is a cross-sectional view of a portion of the apparatus of FIG. 5, constructed in accordance with the present invention, operative for purposes of imparting rotation to a reactor coolant pump motor shaft and the flywheel, taken substantially along the line 6—6 in FIG. 5.
Figure 5:
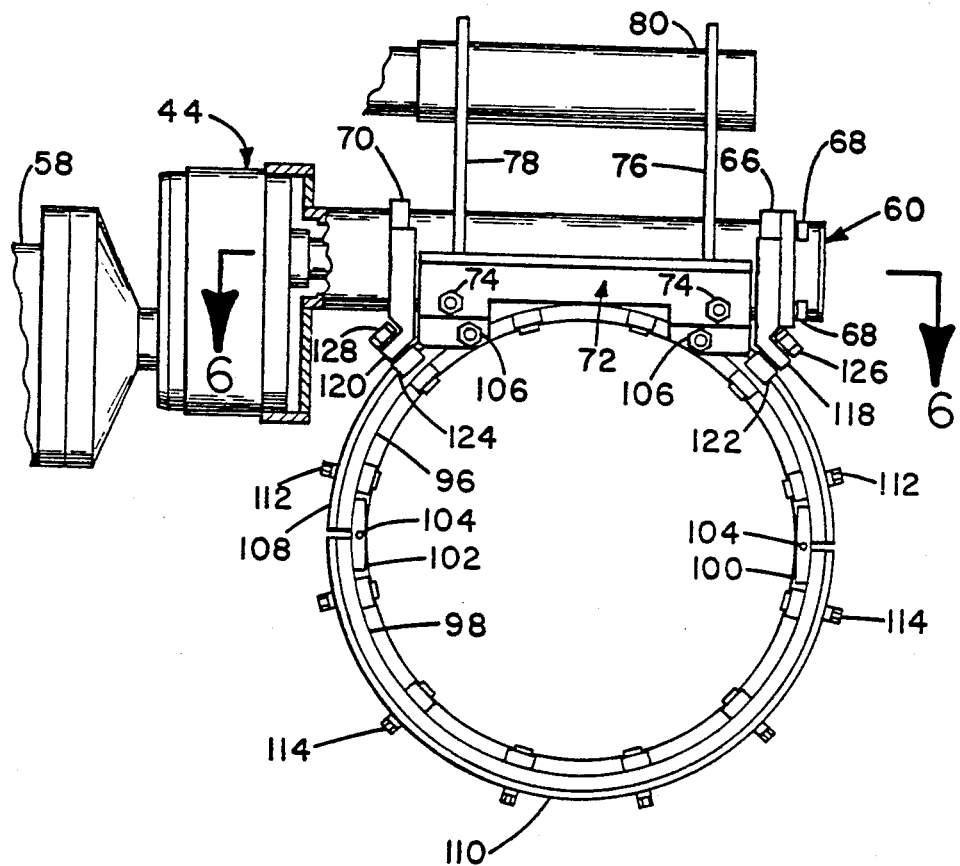
FIG. 5 is a side elevational view on an enlarged scale and with some parts broken away of the apparatus of FIG. 4, constructed in accordance with the present invention, operative for purposes of imparting rotation to a reactor coolant shaft and the flywheel.

Turning now to a consideration of FIGS. 4, 5 and 6 of the drawing, there is depicted therein a second embodiment of an apparatus, the latter being denoted therein generally by the reference numeral 42. The apparatus 42 constructed in accordance with the present invention, like the apparatus 10 of FIGS. 1, 2 and 3, is suited for use for purposes of effecting the rotation of a member such as the shaft 16 of the reactor coolant pump motor 12 of FIG. 1.

Proceeding with a description of the nature of the construction of the apparatus 42, the latter as seen with reference to FIGS. 4, 5 and 6 embodies the following major components: housing means, denoted generally by the reference numeral 44; ring and gear means, denoted generally by the reference numeral 46; shaft means, denoted generally by the reference numeral 48; and clamp and sleeve means, denoted generally by the reference numeral 50. With respect first to the housing means 44, the latter functions as an enclosure for the shaft means 48 as well as serving as the means by which the interengagement of the other major components that comprise the apparatus 42 is effected. To this end, the housing means 44 includes an elongated member 52 suitably configured and dimensioned so as to permit the shaft means 48 to be received therewithin in the manner depicted in FIG. 6 of the drawing, and to which further reference will be had hereinafter. At the lower end thereof, as viewed with reference to FIG. 6, the elongated member 52 has affixed thereto through the use of any suitable conventional form of fastening means (not shown) a cylindrical cup-like member 54. Although not shown in the drawing in the interest of maintaining clarity of illustration therein, the member 54 is preferably affixed to the elongated member 52 by virtue of being welded thereto. The cup-like member 54 in turn is suitably configured so as to permit a speed reducer, designated in the drawing by the reference numeral 56, to be cooperatively associated therewith. More specifically, a portion of the speed reducer 56, as shown in FIGS. 5 and 6, is designed to be inserted into the interior of the cup-like member 54. Moreover, when the speed reducer 56 is so positioned relative to the cup-like member 54, the former preferably is retained in place relative to the latter through the use of a plurality of suitably located, conventionally constructed, threaded fasteners (not shown). For a purpose yet to be described, the speed reducer 56 is operatively connected to an electric motor, the latter being seen at 58 in the drawing. In accord with the best mode embodiment of the apparatus 42, the electric motor 58 comprises a commercially available ½ HP motor. Similarly, the speed reducer 56 comprises a commercially available speed reducer compatible for use with a ½ HP electric motor.

At its other end, the elongated member 52 has suitably mounted thereon a cap assembly, generally designated by the reference numeral 60. The cap assembly 60, in a manner yet to be described, essentially forms an enclosure for one end of the shaft means 48. In this regard, the cap assembly 60 embodies substantially the configuration of an inverted cup. To this end, the cap assembly 60 includes a generally cylindrical member 62 consisting of a body portion 62a from which there projects a flange-like portion 62b. Without departing from the essence of the invention, the generally cylindrical member 62 may comprise either an integral member wherein the flange-like portion 62b is formed integrally with the body portion 62a, or flange-like portion 62b may be formed separately of the body portion 62a and simply thereafter be attached thereto through the use of any conventional form of attaching means suitable for use for this purpose. Lastly, the cap assembly 60 preferably includes an end cap denoted in the drawing by the reference numeral 64, which is suitably configured so that when placed in juxtaposed relation to the body portion 62a is operative to effect the closure, in the manner depicted in FIG. 6, of the otherwise open end of the body portion 62a opposite that whereat the flange-like portion 62b is joined to the latter.

Continuing, for a purpose yet to be described a first side bearing mount, denoted generally by the reference numeral 66, is supported in surrounding relation to the elongated member 52 and in juxtaposed relation to the flange-like portion 62b of the cap assembly 60. In accord with the illustrated embodiment of the apparatus 42, the first side bearing mount 66 is secured to the flange-like portion 62b by means of a plurality of threaded fasteners 68 of a conventional nature. At the other end of the elongated member 52, there is suitably mounted a second side bearing mount, the latter being designated generally in the drawing by the reference numeral 70. Although not depicted in the drawing in the interest of maintaining clarity of illustration therein, the second side bearing mount 70 is suitably secured in place relative to the elongated member 52 through the use of one or more conventional threaded fasteners (not shown).

In a manner best understood with reference to FIG. 5, a support member, generally designated by the reference numeral 72, is suitably mounted on the elongated member 52 of the housing means 44. More specifically, the support member 72 is suitably dimensioned so as to have a length which is essentially coextensive with that portion of the elongated member 52 that extends between the first side bearing mount 66 and the second side bearing mount 70. Further, as seen with reference to FIG. 5 of the drawing, a plurality of cam followers, denoted therein by the reference numeral 74, are suitably mounted relative to the support member 72 so as to be suitably positioned whereby the cam followers 74 are capable of riding along the upper surface, as viewed with reference to FIG. 5, of the ring and gear means 46. In this connection, the aforementioned cam followers 74, the yet to be described cam followers 106, the yet to he described cam follower bearings 122 and 124, and the ring and gear means 46 with which thn former are cooperatively associated collectively comprise another form of drive means, other than the bearing means 26 depicted in FIG. 3, which is operative for purposes of imparting rotation to the shaft 16.

Projecting outwardly from the support member 72 and at substantially right angles thereto are a pair of leg-like members 76 and 78. The leg-like members 76 and 78 are suitably secured at one end thereof to the support member 72 through the use of any suitable conventional form of means of fastening (not shown) such as by being welded thereto. The other end of each of the leg-like members 76 and 78 is cooperatively associated with a member 80, the latter embodying essentially a tubular configuration. For purposes of accomplishing the joinder of the tubular member 80 to the ends of the leg-like members 76 and 78, the former may be welded to the latter. The tubular member 80 in turn is suitably dimensioned internally so as to be capable of receiving one end of a handle 82 therewithin with a friction fit. It is to be understood, however, that the joinder of the end of the handle 82 to the tubular member 80 could be accomplished other than by virtue of the existence of a friction fit therebetween. Namely, this joinder could also, without departing from the essence of the present invention, be effected through the existence of a threaded engagement therebetween. To this end, the inner surface of the tubular member 80 as well as the outer surface of the handle 82 would each have to be suitably provided with threads. As best understood, with reference to FIG. 4, the other end of the handle 82 is operatively connected to the clamp and sleeve means 50.

With further reference to FIG. 4, the clamp and sleeve means 50 includes a sleeve member 84 of tubular configuration and having an interior, which is suitably dimensioned so as to be capable of receiving therewithin with a frictional fit the other end of the handle 82. The clamp and sleeve means 50 also encompasses an essentially U-shaped clamping member 86. In accord with the illustration thereof in FIG. 4 of the drawing, the clamping member 86 is suitably clamped to a member such as the wall of the housing of a reactor coolant pump, the member, e.g., pump housing wall being designated in FIG. 4 by the reference numeral 88. For purposes of securing the clamping member 86 in clamped relation to the pump housing wall 88, there may be employed any suitable conventional form of fastening means such as the threaded fastener seen at 90 in FIG. 4. The threaded fastener 90 shown in FIG. 4 is of the adjustable type such that through the rotation thereof the pump housing wall 88 is caused to become clamped between the end of the threaded fastener 90 and a suitable abutment 92 with which the clamping member 86 is suitably provided. The interconnection of the clamping member 86 and the sleeve member 84 is preferably effected through pivot means of a conventional nature, the latter being identified in FIG. 4 by the reference numeral 94. As such the clamping member 86 and the sleeve member 84 can pivot relative to one another about the pivot means 94. In accord with the aforedescribed construction and to which further reference will again be had hereinafter, the handle 82 and clamp and sleeve means 50 cooperate one with another to resist the tendency of the housing means 44 to rotate with the shaft 16 when rotation is being imparted to the latter in a manner that has yet to be described.

Directing attention to the ring and gear means 46, the ring portion of the latter includes a pair of semicircular ring segments 96, 98. The ring segments 96, 98 are suitably dimensioned so that when joined together in a manner yet to be described they define a circumference that is substantially equal to that member, e.g., the reactor coolant pump motor shaft 16, about which the apparatus 42 is designed to be clamped for purposes of imparting rotation thereto. In accord with the illustrated embodiment thereof, the ring segments 96, 98 are joined together through the use of a pair of members seen at 100 and 102 in FIG. 5. The members 100 and 102 function to effect an interconnection of the ends of the ring seoments 96 and 98, and are in turn secured thereto by means of conventional fasteners denoted in FIG. 5 by the reference numeral 104. In addition, as best understood with reference to FIG. 5, cam followers, denoted therein by the reference numeral 106, are suitably secured to the support member 72 so as to be suitably positioned relative to the ring and gear means 46 so as to be capable of riding along the upper surface thereof as viewed with reference to FIG. 5. By virtue of the fact that the ring segment 96 is fastened to the support member 72, and the ring segment 98 is interconnected by the members 100 and 102 to the ring segment 96, the ring segment 98 is thus also secured to the support member 72.

Continuing, cooperatively associated with the ring segments 96, 98 is a gear means. The latter gear means in accord with the best mode embodiment of the apparatus 42 comprises a pair of gear segment 108 and 110 which are essentially coterminous with the ring segments 96 and 98, respectively. Further, the gear segment 108 is preferably retained in place relative to the ring segment 96 through the use of any suitable conventional form of retention means such as the plurality of threaded fasteners seen at 112 in FIG. 5. Likewise, the gear segment 110 is preferably retained in place relative to the ring segment 98 through the use of any suitable conventional form of retention means such as the plurality of threaded fasteners seen at 114 in FIG. 5. When the ends of the ring segments 96 and 98 are interconnected by means of the members 100 and 102, and the ring segment 96 is secured to the support members 72 in the manner that is depicted in FIG. 5, the gear segments 108 and 110 are suitably positioned relative to the shaft means 48 such as to be engageable with the qear means 116 with which the shaft means 48 is suitahly provided, to which further reference will be had hereinafter. Completing the description of the housing means 44 and the ring and gear means 46, the first side bearing mount 66 and the second side bearing mount 70 are each provided with cam follower means designated by the reference numerals 118 and 120, respectively, in FIG. 5. The cam follower means 118 and 120 each include a cam follower bearing 122 and 124, respectively, and a threaded fastener 126 and 128, respectively. The threaded fasteners 126 and 128 function to secure the cam follower bearings 122 and 124 to the first side bearing mount 66 and the second side bearing mount 70, respectively. With the cam follower bearings 122 and 124 positioned as shown in FIG. 5, they like the cam followers 74 and 106 to which reference has previously been had herein before are suitably located so as to be capable of riding along the upper surface, as viewed with reference to FIG. 5, of the ring and gear means 46.

Considering next the shaft means 48, the latter includes an elongated shaft 130, which has one end thereof suitably dimensioned so as to be receivable, as best understood with reference to FIG. 6, within an opening 132 provided for this purpose in the speed reducer 56. In order to effect the interconnection of the shaft 130 to the speed reducer 56, key means of a conventional nature, seen at 134 in FIG. 6, may be utilized for this purpose. At its other end, the shaft 130 has bearing means 138 positioned thereon. More specifically, as best understood with reference to FIG. 6 the bearing means 138 is interposed between the shaft 130 and a seat with which the inner surface of the elongated member 52 is suitably provided. Further, the upper end of the shaft 130 as viewed with reference to FIG. 6 is suitably threaded such as to receive in threaded engagement therewith a nut 140. The nut 140 is operative to retain the bearing means 138 in position on the shaft 130. To this end, a spacer 142 preferably is also interposed between the nut 140 and the bearing means 138. Finally, the shaft 130 is provided intermediate its length with gear means 116 to which reference has previously been had hereinbefore. The gear means 116 may be cooperatively associated with the shaft 130 in any known fashion so that the gear means 116 is operative to rotate with the shaft 130 and to engage the gear segments 108 and 110 whereby through such engagement rotation is imparted from the shaft 130 to the gear segments 108 and 110 and therethrough to the shaft 16, i.e., the member encircled by the ring and gear means 46 of the apparatus 42.

In accord with the illustration thereof in FIGS. 5 and 6, the first side bearing mount 66, the second side bearing mount 70 and the support member 72 all comprise separate members. However, it is also possible without departing from the essence of the invention and as depicted in FIG. 4 of the drawing to form the first side bearing mount 66, the second side bearing mount 70 and the support member 72 as a single member, the latter being denoted by the reference numeral 144 in FIG. 4. Likewise, the leg-like members 76 and 78, which as depicted in FIG. 5 of the drawing, comprise individual members may also take the form, without departing from the essence of the invention, of members that are joined together by means of a central portion, the latter being denoted by the reference numeral 146 in FIG. 4.

A description will now be had of the mode of operation of the apparatus 42 constructed in accordance with the illustration thereof as found in FIGS. 4, 5 and 6 of the drawing. As set forth previously herein, the apparatus 42 is intended to be employed for purposes of imparting rotation to a component. To this end, the apparatus 42 is particularly suited to being employed for purposes of imparting rotation to the shaft 16 of a reactor coolant pump motor 12, of the type shown in FIG. 1 of the drawing. In order to effect the assembly of the apparatus 42 to the shaft 16, at least one end of each of the ring segments 96 and 98 must be disengaged one from another. This is in order to permit the ring segments 96 and 98 to be passed into surrounding relation around the shaft 16. That is, one of the members 100 or 102 may be disconnected from the ring segments 96 and 98, while the other of the members 100 or 102 is loosened sufficiently so as to enable the ring segments 96 and 98 to move relative to one another. Once the ring segments 96 and 98 have been positioned in encircling relation to the shaft 16, the former are once again interconnected such as to effectuate the clamping of the shaft 16 therebetween. The next step is to secure the clamp and sleeve means 50 to the pump housing wall 88.

This is accomplished by positioning the clamping member 86 of the clamp and sleeve means 50 in juxtaposed relation to the pump housing wall 88 and thereafter by suitably manipulating the fastener 90 effecting the clamping of the pump housing wall 88 between the fastener 90 and the abutment 92. Once the ring segments 96 and 98 are located in clamping relation to the shaft 16 and the clamp and sleeve means 50 has been clamped to the pump housing wall 88, the electric motor 58 may be energized such that rotation is imparted therefrom through the speed reducer 56 to the shaft 130. Rotation of the shaft 130 is in turn transmitted through the gear means 116 with which the former is suitably provided to the gear segments 108 and 110, and therefrom to the shaft 16 by virtue of the fact that the gear segments 108 and 110 are secured to the ring segments 96 and 98 such as to form a unitary structure therewith, while the ring segments 96 and 98 are in turn clamped about the shaft 16. Any tendency on the part of the housing means 44, the speed reducer 56 and the electric motor 58 to rotate along with the shaft 16 is resisted by virtue of the fact that the clamp and sleeve means 50 is clamped to the pump housing wall 88 and is also interconnected to the housing means 44 through the handle 82. To effect the disassembly of the apparatus 42 from the shaft 16, the clamp and sleeve means 50 is simply disconnected from the pump housing wall 88 through the manipulation of the fastener 90, and the ring segments 96 and 98 are removed from encircling relation relative to the shaft 16 through suitable manipulation of one or both of the members 100 and 102.

Thus, in accordance with the present invention there has been provided a new and improved apparatus, which is operative for purposes of effecting relative motion between a component and another device. Moreover, the apparatus of the present invention for purposes of effecting relative motion between a component and another device is operative to impart rotation to the component. In addition, in accord with the present invention an apparatus is provided which is particularly suited for use for purposes of imparting rotation to a component wherein the component is required to be rotated in order to conduct an examination thereof. Further, the apparatus of the present invention is particularly suited for use for purposes of effecting the rotation of the reactor coolant pump motor and flywheel in order that an examination may be conducted thereof. Additionally, in accordance with the present invention an apparatus operative for purposes of imparting rotation to a reactor coolant pump motor and flywheel is provided, which is characterized in that a constant speed of rotation is capable of being imparted therewith. Furthermore, the apparatus operative for purposes of imparting rotation to a reactor coolant pump motor and flywheel of the present invention is characterized in that it is relatively easy to install, relatively simple to operate, yet is relatively inexpensive to provide.

While only one embodiment of my invention has been shown, it will be appreciated that modifications thereof, some of which have been alluded to hereinabove, may still be readily made thereto by those skilled in the art. I, therefore, intend by the appended claims to cover the modifications alluded to herein as well as all other modifications which fall within the true spirit and scope of my invention.

What is claimed is:

1. An apparatus for imparting rotation to a member supported for rotation within a surrounding housing comprising:
   (a.) a first semicylindrical segment embodying a first split ring ball bearing including a first inner diameter race and a first outer diameter race, said first inner diameter race and said first outer diameter race being cooperatively associated one with another so as to enable relative motion to occur therebetween;
   (b.) a second semicylindrical segment embodying a second split ring ball bearing including a second inner diameter race and a second outer diameter race, said second inner diameter race and said second outer diameter race being cooperatively associated one with another so as to enable relative motion to occur therebetween;
   (c.) hinge means pivotably interconnecting one end of said first semicylindrical segment with one end of said second semicylindrical segment so as to enable said first and second semicylindrical segments to pivot relative to one another between an open position to permit the member to be rotated to be inserted therebetween and a closed position to permit the member to be rotated to be clamped therebetween;
   (d.) detachable fastening means securing the other end of said first semicylindrical segment to the other end of said second semicylindrical segment when the member to be rotated is encircled by said first and second semicylindrical segments;
   (e.) first gear means including a two piece driven gear, one piece of said two piece driven gear being operatively connected to said first semicylindrical segment and the other piece of said two piece driven gear being operatively connected to said second semicylindrical segment;
   (f.) second gear means operatively connected to said first gear means for driving said first gear means and thereby said first and second semicylindrical segments when said second gear means is being driven;
   (g.) motor means operatively connected to said second gear means, said motor means when energized being operative to effect rotation of said second gear means, said second gear means when rotated by said motor means effecting the rotation of said first gear means and therethrough the rotation of the member clamped between said first and second semicylindrical segments; and
   (h.) an antirotation member having one end thereof secured to one of said first and second semicylindrical segments such that said antirotation member projects outwardly from said one of said first and second semicylindrical segments in a radial direction relative thereto and in substantially parallel relation to said motor means, said antirotation member having the other end thereof positioned in abutting engagement with the housing surrounding the member to be rotated such that the interengagement of said other end of said antirotation member with the housing surrounding the member to be rotated prevents said motor means from rotating along with the member to be rotated when the member to be rotated is being rotated.

2. An apparatus for imparting rotation to a member supported for rotation within a surrounding housing comprising:

(a.) a first semicylindrical segment having an internal configuration complementary to the external configuration of a first portion of the member to be rotated;

(b.) a second semicylindrical segment having an internal configuration complementary to the external configuration of the remaining portion of the member to be rotated;

(c.) first fastening means fastening one end of said first semicylindrical segment to one end of said second semicylindrical segment so as to permit the insertion of the member to be rotated between said first and second semicylindrical segments;

(d.) second fastening means securing the other end of said first semicylindrical segment to the other end of said second semicylindrical segment when the member to be rotated is encircled by said first and second semicylindrical segments;

(e.) first gear means operatively connected to said first semicylindrical segment and to said second semicylindrical segment;

(f.) second gear means operatively connected to said first gear means for driving said first gear means;

(g.) cam follower means supported on said second gear eans, said cam follower means being located so as to be engageable with at least one surface of each of said first and second semicylindrical segments;

(h.) motor means operatively connected to said second gear means, said motor means when energized being operative to effect rotation of said second gear means, said second gear as said cam follower means traverses said at least one surface of each of said first and second semicylindrical segments of said first gear means and therethrough the rotation of the member clamped between said first and second semicylindrical segments; and (i.) antirotation means operative to prevent said motor means from rotating along with the member to be rotated when the member to be rotated is being rotated, said antirotation means including an antirotation member and clamp and sleeve means, said antirotation member having one end thereof supported from said first gear means such that said antirotation member projects outwardly from said first gear means in substantially parallel relation to said motor means, said antirotation means having the other end thereof received by said clamp and sleeve means, said clamp and sleeve means including a clamp for clamping said clamp and sleeve means and thereby said antirotation member to the housing surrounding the member to be rotated to prevent relative movement therebetween.

3. The apparatus as set forth in claim 2 further comprising speed reducer means interposed in operative relation between said motor means and said second gear means.

* * * * *